United States Patent
Brown et al.

(10) Patent No.: US 8,313,711 B2
(45) Date of Patent: Nov. 20, 2012

(54) LIQUID DISPENSING FOR HIGH-THROUGHPUT EXPERIMENTATION

(75) Inventors: Jeffrey A. Brown, San Carlos, CA (US); Hyeok Hahn, Santa Clara, CA (US); Peter Calcavecchio, Milford, NJ (US); Jason Gao, Rose Valley, PA (US)

(73) Assignee: Freeslate, Inc., Sunnyvale, CA (US)

( * ) Notice: Subject to any disclaimer, the term of this patent is extended or adjusted under 35 U.S.C. 154(b) by 1034 days.

(21) Appl. No.: 12/088,769

(22) PCT Filed: Oct. 30, 2006

(86) PCT No.: PCT/US2006/042673
§ 371 (c)(1), (2), (4) Date: Oct. 23, 2008

(87) PCT Pub. No.: WO2007/053692
PCT Pub. Date: May 10, 2007

(65) Prior Publication Data
US 2009/0220385 A1  Sep. 3, 2009

Related U.S. Application Data

(60) Provisional application No. 60/732,274, filed on Nov. 1, 2005.

(51) Int. Cl.
*B01F 15/02* (2006.01)
*B01F 3/00* (2006.01)

(52) U.S. Cl. ..... 422/501; 422/521; 366/138; 366/177.1; 366/181.8

(58) Field of Classification Search ............... 366/177.1, 366/366, 138, 181.8; 422/522, 521, 505, 422/504, 501, 500, 63
See application file for complete search history.

(56) References Cited

U.S. PATENT DOCUMENTS

| | | | | |
|---|---|---|---|---|
| 5,525,302 A | * | 6/1996 | Astle | 422/511 |
| 5,736,105 A | * | 4/1998 | Astle | 422/509 |
| 5,935,859 A | * | 8/1999 | Elliott et al. | 506/33 |
| 6,060,320 A | * | 5/2000 | Dorenkott et al. | 436/54 |
| 6,232,129 B1 | * | 5/2001 | Wiktor | 436/180 |
| 6,260,407 B1 | * | 7/2001 | Petro et al. | 73/61.52 |
| 6,265,226 B1 | * | 7/2001 | Petro et al. | 506/12 |
| 6,345,528 B2 | * | 2/2002 | Petro et al. | 73/61.52 |

(Continued)

FOREIGN PATENT DOCUMENTS
AU        622480 B        3/1990
(Continued)

OTHER PUBLICATIONS

International Search Report and Written Opinion issued in PCT/US06/042673 dated Feb. 23, 2007, 11 pages.

(Continued)

*Primary Examiner* — Tony G Soohoo
(74) *Attorney, Agent, or Firm* — Armstrong Teasdale LLP

(57) ABSTRACT

Methods, systems, and apparatus, including computer program products, implementing techniques for mixing liquid components. Quantities of two or more liquid components are transferred from pressurized source reservoirs to one or more destination locations by means of a fluid outlet that includes a dispense valve, and the two or more liquid components are mixed in the destination locations to create a plurality of fluid mixtures. Two or more dispensing technologies can be combined to provide for increased efficiency in the dispensing of high volume liquid components. The amounts of liquid components being dispensed can be monitored during the dispensing to provide feedback control of the dispensing.

12 Claims, 6 Drawing Sheets

U.S. PATENT DOCUMENTS

| | | | |
|---|---|---|---|
| 6,406,632 B1* | 6/2002 | Safir et al. ............... | 506/7 |
| 6,464,385 B2 | 10/2002 | Akimoto | |
| 6,554,162 B2 | 4/2003 | Schell | |
| 6,818,060 B2 | 11/2004 | Stewart | |
| 7,459,126 B2* | 12/2008 | Okun ........................ | 422/63 |
| 7,588,725 B2* | 9/2009 | Ozbal et al. ............... | 422/63 |
| 2001/0027949 A1* | 10/2001 | Safir et al. ................ | 210/635 |
| 2004/0136873 A1* | 7/2004 | Meier ........................ | 422/99 |
| 2004/0136878 A1* | 7/2004 | Meier et al. ............... | 422/102 |
| 2004/0163730 A1* | 8/2004 | Olson et al. ............... | 141/130 |
| 2004/0202573 A1* | 10/2004 | van den Brink et al. ... | 422/68.1 |
| 2004/0219069 A1* | 11/2004 | Kalra et al. ................ | 422/99 |
| 2004/0265185 A1 | 12/2004 | Kitagawa | |
| 2005/0194318 A1* | 9/2005 | Ozbal et al. ............... | 210/656 |
| 2006/0002824 A1* | 1/2006 | Chang et al. .............. | 422/100 |
| 2006/0228265 A1* | 10/2006 | Peng et al. ................ | 422/102 |
| 2009/0220385 A1* | 9/2009 | Brown et al. .............. | 422/100 |
| 2011/0124111 A1* | 5/2011 | Hoshizaki et al. ......... | 436/94 |

FOREIGN PATENT DOCUMENTS

EP  1260435 A1  11/2002

OTHER PUBLICATIONS

Supplemental Search Report from Related EP national phase application No. 06836764.8, issued Oct. 19, 2009, 5 pages.

* cited by examiner

LIQUID DISPENSING FOR HIGH-THROUGHPUT EXPERIMENTATION

BACKGROUND

This invention relates to techniques for dispensing liquids and formulating liquid mixtures. Automated systems for conducting high-throughput experimentation typically include liquid and/or solid dispensing technology that is capable of dispensing and mixing components in varying proportions and in precise, microscale quantities in a substrate, such as a microtiter plate, to prepare libraries of different materials on a miniaturized scale, creating hundreds to thousands of experiments at a time. The library is then processed under controlled conditions to produce a desired collection of materials. The library may then be screened for any of a variety of physical, chemical or functional properties to identify promising candidates for a target application.

Conventional automated high-throughput dispensing systems are typically intended for application in a specific field, such as biotechnology or catalyst research. These systems are therefore often designed to perform well under a limited range of conditions, and with a limited range of materials, that are expected to be relevant to typical experiments in the intended field. But the performance of these systems may suffer when they are confronted with conditions outside of their optimal performance domain—for example, dispensing in higher volumes than typical micro-scale high-throughput experimentation—or with materials that have properties that are significantly different from typical materials in their application domain. As a result, there remains a need for dispensing and blending techniques that are capable of performing quickly and accurately over a broad range of operating conditions.

SUMMARY

The invention provides methods and apparatus implementing techniques for dispensing and blending liquids. In general, in one aspect, the invention features methods, systems, and apparatus, including computer program products, implementing techniques for mixing liquid components. The techniques include providing a plurality of source reservoirs, pressurizing one or more of the plurality of source reservoirs, transferring a quantity of a first liquid component from a first pressurized source reservoir to one or more destination locations by means of a fluid outlet that includes a dispense valve, transferring a quantity of a second liquid component from a second pressurized source reservoir to the one or more destination locations through the dispense valve, and mixing the first and second liquid components in the destination locations to create a plurality of fluid mixtures. The fluid outlet is positionable to dispense the liquid components through the dispense valve into the one or more destination locations.

Particular implementations can include one or more of the following features. The second liquid component can be transferred without exposing the second liquid component to the first liquid component. Transferring the first liquid component can include introducing the first liquid component at a first inlet into a conduit network that defines a flow path from the first inlet and a second inlet to the fluid outlet. Transferring the second liquid component can include introducing the second liquid component at the second inlet into the conduit network. The techniques can include flushing the conduit network and the fluid outlet with a cleaning fluid after transferring the first liquid component to prevent contamination of the second liquid component by the first liquid component. Flushing the conduit network can include introducing the cleaning fluid into the conduit network and transporting the cleaning fluid along the flow path from the first inlet to the fluid outlet. The conduit network can have substantially no dead space in the flow path from the first inlet to the fluid outlet. Introducing the cleaning fluid can include introducing the cleaning fluid at the first inlet into the conduit network, or at a third inlet into the conduit network that is upstream from the first inlet.

The techniques can include transferring a quantity of one or more third liquid components from one or more third reservoirs of the plurality of source reservoirs to one or more of the destination locations through the dispense valve. The one or more third liquid components can be transferred without exposing any one of the one or more third liquid components to any of the first liquid components, second components, or others of the one or more third liquid components. Transferring the one or more third liquid components can include introducing the one or more third liquid component at one or more fourth inlets into the conduit network, where the conduit network defines a flow path from each of the one or more fourth inlets to the fluid outlet. Before the one or more fourth liquid components are transferred, the conduit network and the fluid outlet can be flushed with a cleaning fluid to prevent contamination of the corresponding one of the third liquid components by any of the second liquid component or others of the one or more third liquid components.

The conduit network can include a plurality of three-way valves configured to define a hierarchical flow path from each of a plurality of inlets associated with the plurality of source reservoirs to the fluid outlet. The conduit network can have substantially no dead space in the hierarchical flow path from any of the plurality of inlets to the fluid outlet. The transferring can include transferring at least five, at least 10, at least 15, or at least 20 different liquid components to locations in the one or more destination locations. The transferring and mixing can include comprise dispensing and mixing quantities of the first and second liquid components in at least six, at least 12, at least 24, at least 48, or at least 96 destination locations to create at least six, at least 12, at least 24, at least 48, or at least 96 fluid mixtures.

The transferring can include sequentially positioning the fluid outlet to dispense a corresponding component into each of a plurality of wells in a destination array. The transferring can include measuring the quantity of the corresponding liquid component being transferred to the one or more destination locations. Measuring the quantity can include measuring, during the transferring, the weight or mass of the corresponding liquid component being transferred. The transferring can be controlled based on the measured quantity of the first, second or third component.

The techniques can include, before transferring a given liquid component of the plurality of liquid components to the one or more destination locations, generating a calibration for the given liquid component by determining a range of volumes of the given liquid component to be dispensed to locations in the one or more destination locations, performing a plurality of dispenses of the given liquid component, including, for each of the plurality of dispenses, activating the dispense valve for a time period corresponding to a volume in the determined range of volumes, measuring a quantity of the given liquid component dispensed in each of the plurality of dispenses, and calculating a calibration curve for the given liquid component based on the time periods and the measured quantities of the given liquid component for each of the plurality of dispenses. Transferring the given liquid component can include, for each destination location into which the given liquid component will be dispensed, calculating a dispense interval based on a desired quantity of the given liquid component and the calibration curve and activating the dispense valve for the calculated dispense interval to dispense the given liquid component.

Transferring the given liquid component can include activating the dispense valve for a first dispense interval corresponding to a first desired quantity of the given liquid component that is less than a target quantity of the given liquid component and measuring a quantity of the given liquid component dispensed during the first dispense interval, calculating a second dispense interval based on the measured quantity and the target quantity of the given liquid component, activating the dispense valve for the second dispense interval and measuring a quantity of the given liquid component dispensed during the second dispense interval, and repeating the calculating and the activating until an amount of the given liquid component that is within a predetermined amount of the target quantity of the given liquid component is dispensed. The second dispense interval can correspond to a second desired quantity of the given liquid component that is less than the difference between the target quantity and the first desired quantity.

The techniques can include transferring a quantity of one or more fourth liquid components from one or more fourth source reservoirs of the plurality of source reservoirs to one or more of the plurality of destination locations using a syringe pump or a positive displacement pump. The fourth liquid components are dispensed at one or more of the destination locations in volumes ranging from about 0.1% to about 5% of a total volume dispensed at one or more of the destination locations and the first liquid component and the second liquid component are dispensed at one or more of the destination locations in volumes ranging from about 50% to about 90% of the total volume dispensed at the one or more of the destination locations. Pressurizing one or more of the source reservoirs can include independently pressurizing a plurality of the source reservoirs to provide for a target flow rate of the corresponding liquid components at the dispense valve.

In general, in another aspect, the invention features a system for dispensing liquids. The system includes a plurality of pressurizable source reservoirs, each containing a liquid component and being operable to maintain an elevated pressure for forcing the corresponding liquid component to exit the source reservoir, one or more destination substrates having one or more destination locations for receiving liquid components to prepare one or more liquid mixtures, a conduit network comprising a plurality of inlets associated with the pressurizable source reservoirs and defining a flow path from each of the plurality of inlets, a first fluid outlet for receiving liquid components through the flow path from each of the plurality of inlets, the first fluid outlet comprising a common dispense valve and being positionable to dispense the received liquid components through the common dispense valve into any of the one or more destination locations, and a control system operable to control the first fluid outlet and the common dispense valve to position the first fluid outlet and activate the common dispense valve for dispensing liquid components at the one or more destination locations.

Particular implementations can include one or more of the following features. The source reservoirs can be independently pressurized to provide for a target flow rate of the corresponding liquid components at the dispense valve. The conduit network can include substantially no dead space in the flow path from any one of the plurality of inlets to the first fluid outlet. The system can include a cleaning fluid reservoir in fluid communication with the conduit network. The cleaning fluid reservoir can be positioned and configured to introduce a cleaning fluid into the conduit network to flush the flow path from any one of the plurality of inlets. The cleaning fluid reservoir can be fluidically coupled to the conduit network at each of the plurality of inlets associated with the plurality of pressurizable source reservoirs. The conduit network can include a cleaning fluid inlet located upstream from each of the plurality of inlets associated with the source reservoirs. The control system can be operable to cause the dispensing of quantities of each of a plurality of the liquid components into each of a plurality of the destination locations by, sequentially for each of the plurality of liquid components, activating the inlet associated with the corresponding pressurizable source reservoir to introduce the liquid component into the conduit network, activating the dispense valve to dispense a quantity of the liquid component at the one or more destination locations, and flushing conduit network to prevent contamination of subsequent liquid components by the liquid component.

The conduit network can include a plurality of three-way valves configured to define a hierarchical flow path from each of the plurality of inlets to the first fluid outlet, the conduit network having substantially no dead space in the hierarchical flow path from any of the plurality of inlets to the first fluid outlet. The control system can be operable to control the dispense valve based on a measured quantity of liquid components being dispensed at the one or more destination locations. The system can include one or more balances configured to support the destination substrates. The control system can be configured to receive, from the one or more balances, signals representing the measured quantity of liquid components being dispensed at the one or more destination locations.

The control system can be operable, before dispensing a given liquid component of the plurality of liquid components, to generate a calibration for the given liquid component by determining a range of volumes of the given liquid component to be dispensed to locations in the one or more destination locations, performing a plurality of dispenses of the given liquid component, including, for each of the plurality of dispenses, activating the dispense valve for a time period corresponding to a volume in the determined range of volumes, measuring a quantity of the given liquid component dispensed in each of the plurality of dispenses, and calculating a calibration curve for the given liquid component based on the time periods and the measured quantities of the given liquid component for each of the plurality of dispenses. The control system can be operable to control the dispense valve by, for each destination location into which the given liquid component will be dispensed, calculating a dispense interval based on a desired quantity of the given liquid component and the calibration curve and activating the dispense valve for the calculated dispense interval to dispense the given liquid component. The control system can be operable to control the dispense valve to dispense the given liquid component by activating the dispense valve for a first dispense interval corresponding to a first desired quantity of the given liquid component that is less than a target quantity of the given liquid component and measuring a quantity of the given liquid component dispensed during the first dispense interval, calculating a second dispense interval based on the measured quantity and the target quantity of the given liquid component, the second dispense interval corresponding to a second desired quantity of the given liquid component that is less than the difference between the target quantity and the first desired quantity, activating the dispense valve for the second dispense interval and measuring a quantity of the given liquid component dispensed during the second dispense interval, and repeating the calculating and the activating until an amount of the given liquid component that is within a predetermined amount of the target quantity of the given liquid component is dispensed.

The system can include one or more second source reservoirs containing one or more second liquid components, and a syringe pump or a positive displacement pipette configured to receive the one or more second liquid components for dispensing through a second fluid outlet into the one or more destination locations. The second liquid components can include one or more additives dispensed in volumes ranging from about 0.1% to about 5% of a total volume dispensed at one or more of the destination locations, and the liquid components in the plurality of pressurizable source reservoirs can include one or more base components dispensed in volumes ranging from about 50% to about 90% of the total volume dispensed at the one or more of the destination locations.

The plurality of pressurizable source reservoirs includes at least five, at least 10, at least 15, or at least 20 pressurizable source reservoirs containing at least five, at least 10, at least 15, or at least 20 different liquid components. The destination substrates can include at least six, at least 12, at least 24, at least 48 or at least 96 locations for receiving liquid components. The system can include a liquid handling robot having one or more robotic arms. The first and second fluid outlets can be mounted on the one or more robotic arms. The first fluid outlet can be mounted on a first arm of the one or more robotic arms, and the second fluid outlet can be mounted on a second arm of the one or more robotic arms.

In general, in another aspect, the invention features a system for dispensing fluids. The system includes a liquid handling robot having one or more robotic arms, a plurality of source reservoirs, each containing a liquid component, one or more conduit networks defining one or more flow paths from one or more of the plurality of source reservoirs, one or more destination substrates having one or more destination locations for receiving liquid components to prepare one or more liquid mixtures, a plurality of fluid outlets mounted on the one or more robotic arms, each of the fluid outlets being configured to receive liquid components from one or more of the source reservoirs, the fluid outlets including a first fluid outlet configured to dispense the received liquid components into one or more of the destination locations according to a high-volume dispensing technology and a second fluid outlet configured to dispense the received liquid components into one or more of the destination locations according to a low-volume dispensing technology, and a control system operable to control the liquid handling robot and the first and second fluid outlets to cause the system to dispense the liquid components at the one or more destination locations.

Particular implementations can include one or more of the following features. The high-volume dispensing technology can include a back-pressure dispense technology in which the first fluid outlet includes a dispense valve in fluid communication with a first conduit network of the one or more conduit networks. The first conduit network can include a plurality of inlets, each being associated with one of a first set of source reservoirs, each of the first set of source reservoirs containing a first liquid component and being operable to maintain an elevated pressure for forcing the corresponding liquid component to exit the first source reservoir. The first conduit network can define a flow path from each of the plurality of inlets to the first fluid outlet. The first fluid outlet can be positionable using the one or more robotic arms to dispense the first liquid components through the dispense valve into any of the one or more destination locations.

The second fluid outlet can include or be in fluid communication with a syringe pump or positive displacement pipette. The syringe pump or positive displacement pipette can be in fluid communication with a second set of source reservoirs containing a plurality of second liquid components. The syringe pump or positive displacement pipette can be operable to withdraw one or more of the second liquid components from the second source reservoirs and to dispense the withdrawn second liquid components at the one or more destination locations through the second fluid outlet. The first source reservoirs can be independently pressurized to provide for a target flow rate of the first liquid components at the dispense valve. The first conduit network can include substantially no dead space in the flow path from any one of the plurality of inlets to the first fluid outlet.

The plurality of source reservoirs can include a cleaning fluid reservoir in fluid communication with first conduit network. The cleaning fluid reservoir can be positioned and configured to introduce a cleaning fluid into the first conduit network to flush the flow path from any one of the plurality of inlets. The cleaning fluid reservoir can be fluidically coupled to the first conduit network at each of the plurality of inlets associated with the plurality of first source reservoirs. The first conduit network can include a cleaning fluid inlet located upstream from each of the plurality of inlets associated with the first set of source reservoirs.

The control system can be operable to cause the dispensing of quantities of each of a plurality of the first liquid components into each of a plurality of the destination locations by, sequentially for each of the plurality of first liquid components, activating the inlet associated with the corresponding first source reservoir to introduce the first liquid component into the first conduit network, positioning the first fluid outlet at one or more of the destination locations, activating the dispense outlet to dispense a quantity of the first liquid component at the one or more destination locations, and flushing first conduit network to prevent contamination of subsequent first liquid components by the first liquid component. The first conduit network can include a plurality of three-way valves configured to define a hierarchical flow path from each of the plurality of inlets to the first fluid outlet. The conduit network can have substantially no dead space in the hierarchical flow path from any of the plurality of inlets to the first fluid outlet.

The control system can be operable to control the dispensing of liquid components based on a measured quantity of liquid components being dispensed at the one or more destination locations. The system can include one or more balances configured to support the destination substrates. The control system can be configured to receive, from the one or more balances, signals representing the measured quantity of liquid components being dispensed at the one or more destination locations. The control system can be operable, before dispensing a given first liquid component of the plurality of first liquid components, to generate a calibration for the given first liquid component by determining a range of volumes of the given first liquid component to be dispensed to locations in the one or more destination locations, performing a plurality of dispenses of the given first liquid component, including, for each of the plurality of dispenses, activating the dispense valve for a time period corresponding to a volume in the determined range of volumes, measuring a quantity of the given first liquid component dispensed in each of the plurality of dispenses, and calculating a calibration curve for the given first liquid component based on the time periods and the measured quantities of the given first liquid component for each of the plurality of dispenses. The control system can be operable to control the dispense valve by, for each destination location into which the given first liquid component will be dispensed, calculating a dispense interval based on a desired quantity of the given first liquid component and the calibration curve and activating the dispense valve for the calculated dispense interval to dispense the given first liquid component.

The control system can be operable to control the dispense valve to dispense the given first liquid component by activating the dispense valve for a first dispense interval corresponding to a first desired quantity of the given first liquid component that is less than a target quantity of the given first liquid component and measuring a quantity of the given first liquid component dispensed during the first dispense interval, calculating a second dispense interval based on the measured quantity and the target quantity of the given first liquid component, the second dispense interval corresponding to a second desired quantity of the given first liquid component, the second desired quantity being less than the difference between the target quantity and the first desired quantity, activating the dispense valve for the second dispense interval and measuring a quantity of the given first liquid component dispensed during the second dispense interval, and repeating the calculating and the activating until an amount of the given liquid component that is within a predetermined amount of the target quantity of the given first liquid component is dispensed.

The second liquid components can include one or more additives dispensed in volumes ranging from about 0.1% to about 5% of a total volume dispensed at one or more of the destination locations, and the first liquid components can include one or more base components dispensed in volumes ranging from about 50% to about 90% of the total volume dispensed at the one or more of the destination locations. The plurality of source reservoirs includes at least five, at least 10, at least 15, or at least 20 source reservoirs containing at least five, at least 10, at least 15, or at least 20 different liquid components. The destination substrates can include at least six, at least 12, at least 24, at least 48 or at least 96 locations for receiving liquid components.

In general, in still another aspect, the invention features systems, methods and apparatus, including computer program products, implementing techniques for dispensing liquid components in a system comprising one or more source reservoirs, a conduit network comprising one or more inlets, and a dispense valve, in which each of the inlets is associated with one of the source reservoirs, each of the source reservoirs contains a liquid component, and the conduit network defines a flow path from each of the inlets to the dispense valve. The techniques include: (a) determining a range of volumes of a first liquid component; (b) performing a plurality of dispenses of the first liquid component, including, for each of the plurality of dispenses, activating the dispense valve for a time period corresponding to a volume in the determined range of volumes; (c) measuring a quantity of the first liquid component dispensed in each of the plurality of dispenses; (d) calculating a calibration curve for the first liquid component based on the time periods and the measured quantities of the first liquid component for each of the plurality of dispenses; and (e) storing the calibration curve in a memory.

Particular implementations can include one or more of the following features. The techniques can include: (f) calculating a dispense interval based on a target quantity of the first liquid component and the calibration curve; and (g) activating the dispense valve for the calculated dispense interval to dispense a quantity of the first liquid component at one or more destination locations. Calculating a dispense interval and activating the dispense valve can include activating the dispense valve for a first dispense interval corresponding to a first desired quantity of the given liquid component that is less than the target quantity of the first liquid component and measuring a quantity of the first liquid component dispensed during the first dispense interval, calculating a second dispense interval based on the measured quantity and the target quantity of the first liquid component, the second dispense interval corresponding to a second desired quantity of the first liquid component, the second desired quantity being less than the difference between the target quantity and the first desired quantity, activating the dispense valve for the second dispense interval and measuring a quantity of the first liquid component dispensed during the second dispense interval, and repeating the calculating and the activating until an amount of the given liquid component that is within a predetermined amount of the target quantity of the first liquid component is dispensed. Calculating a dispense interval and activating the dispense valve can include calculating a dispense interval for each of a plurality of dispenses to be performed at a plurality of destination locations, sequentially positioning the dispense valve at each of the plurality of dispense locations, and at each of the plurality of dispense locations, activating the dispense valve for the corresponding dispense interval to dispense a quantity of the first liquid component at the dispense location. The techniques can include repeating steps (a) through (f) for one or more second liquid components to dispense a quantity of the second liquid components at the one or more destination locations.

The invention can be implemented to realize one or more of the following advantages, alone or in the various possible combinations. The use of backpressure dispensing provides for faster dispensing of large volumes of liquids, or of groups of liquids spanning a large viscosity range, with significantly better precision and accuracy than traditional techniques. Many components can be dispensed to a single destination location. The high dispense speed and precision make it possible to dispense relatively large volumes with high accuracy in a high-throughput mode.

The use of an on-line balance makes it possible to incorporate closed-loop, real-time feedback based on the actual dispensed amount of each liquid component. Automated calibration for each liquid component compensates for differing material performance that may result when dispensing materials having significantly different physical properties, and for variations in system performance that may result from equipment wear or environmental conditions.

A single instrument can be used to dispense in significantly different volume regimes—for example, in both small volume high-throughput experimentation and scale up to larger volumes. In particular, the incorporation of two different dispensing technologies in a single instrument allows the system to dispense different volumes in a very efficient manner. More generally, the use of a high-volume dispensing technology can provide for more efficient dispensing of base components and/or common components, while a low-volume dispensing technology can be used to dispense additives and/or uncommon components with minimal material requirements and/or waste. The combination of different dispensing technologies can also make it possible to quickly and accurately dispense both high-viscosity and low-viscosity components with a single instrument.

The incorporation of different dispensing technologies in a single instrument also makes it possible to formulate complex blends without requiring time-consuming transport of materials between workstations, which results in a simpler system that may be easier to operate in an autonomous fashion. Integration of different dispense technologies in a single instrument can provide additional efficiencies by eliminating the need to duplicate resources—for example, since both high-volume and low-volume technologies dispense into the same substrate, only a single substrate, and a single balance, may be required.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Liquid dispensing systems and methods according to one aspect of the present invention implement techniques for dispensing high volume liquids, optionally in combination with complementary techniques for dispensing low volume liquids. In some embodiments, these techniques incorporate real-time feedback control during the dispensing based on ongoing monitoring of the amount—in particular embodiments, the mass or weight—of liquid being dispensed. To facilitate high-throughput and/or combinatorial preparation and screening of liquid mixtures, the techniques described herein can be implemented to provide for dispensing a large number of liquid components to one or many destination locations. These liquid components can be mixed at the various destination locations to produce liquid mixtures, which can then be subjected to a variety of screening techniques.

In particular embodiments, which will be described in more detail below, the systems and methods feature the use of backpressure dispensing technology, in which one or more liquid components are stored in pressure vessels coupled to a network of fluid conduits. The conduit network defines a flow path between each of the pressure vessels and a single dispensing valve that is operated under computer control to meter the dispensing of the liquid into destination locations at which the liquid mixtures will be prepared. The high-speed, automated control of the dispensing valve provides for dispensing of precisely controlled amounts of the liquid components to the destination locations. The conduit network can be constructed to allow for thorough cleaning of the fluid conduits between dispenses of different liquid components to prevent contamination or mixing of the liquid components in the conduit network.

Figure 1:
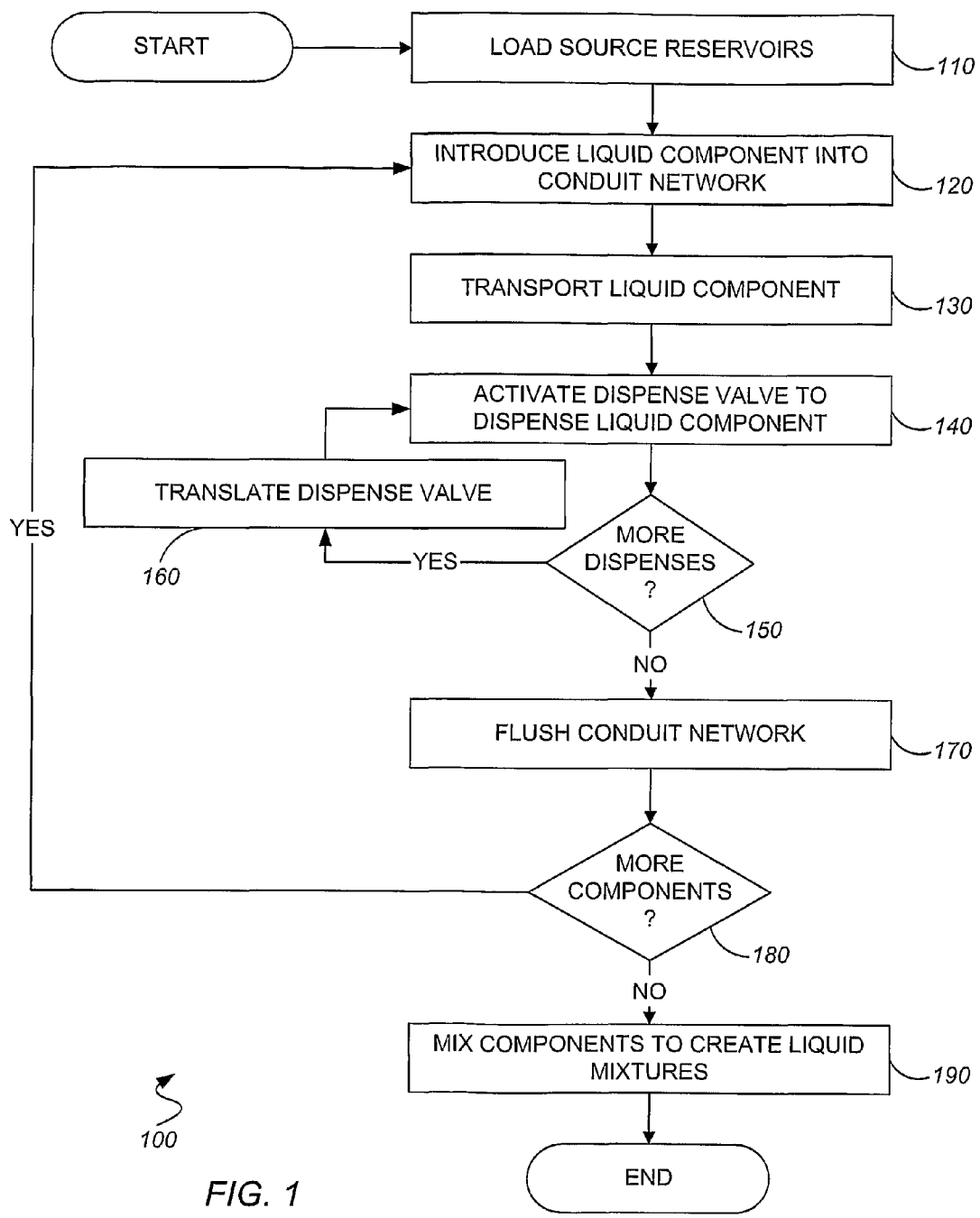
FIG. 1 is a flow diagram illustrating one embodiment of a backpressure dispensing method suitable for dispensing high-volume and/or high-viscosity components according to one aspect of the invention.

Thus, a method 100 for dispensing liquid components to one or more destination locations according to one aspect of the invention is illustrated in FIG. 1. A plurality of pressurized source reservoirs are charged with a plurality of liquid components (step 110). An outlet leading from a first one of the source reservoirs is opened, and a quantity of a first liquid component is forced out of the source reservoir and into a network of fluid conduits by the reservoir pressure (step 120). The conduit network transports the first liquid component along a flow path to a dispense valve positioned at a destination location (step 130). The dispense valve is activated for a specified time interval (step 140) and a portion of the first liquid component is dispensed at the destination location. If the first liquid component is to be dispensed at additional destination locations (the YES branch of step 150), the dispense valve is moved to a different destination location and activated to dispense a portion of the first liquid component at the new location (step 160). When the dispensing of the first liquid component is complete (the NO branch of step 150), the conduit network is flushed with a cleaning fluid or fluids (step 170). If additional liquid components are to be dispensed (the YES branch of step 180), steps 120 through 170 are repeated for each additional liquid component, and the additional liquid components are dispensed through the dispense valve at the desired destination locations. When the dispensing of all liquid components is complete (the NO branch of step 180), the liquid components at each destination location are mixed to form a plurality of liquid mixtures (step 190) and the method ends.

According to one aspect of the present invention, one or more systems, methods or both are used to assist in dispensing various liquid components to form libraries of liquid mixtures. Though manual or semi-automated systems and methods are possible, preferably an automated system or method is employed, in which a robotic or automatic system automatically or programmably implements a sequence of predetermined motions for handling, contacting, dispensing, or otherwise manipulating materials in solid, liquid or gas form to prepare liquid mixtures satisfying a set of predetermined recipes according to a predetermined protocol. Exemplary robotic systems are commercially available from Tecan Systems, Inc. (e.g., RSP 9000 Robotic Sample Processor) or Denso Corporation (e.g., VP Series Robot).

Figure 2:
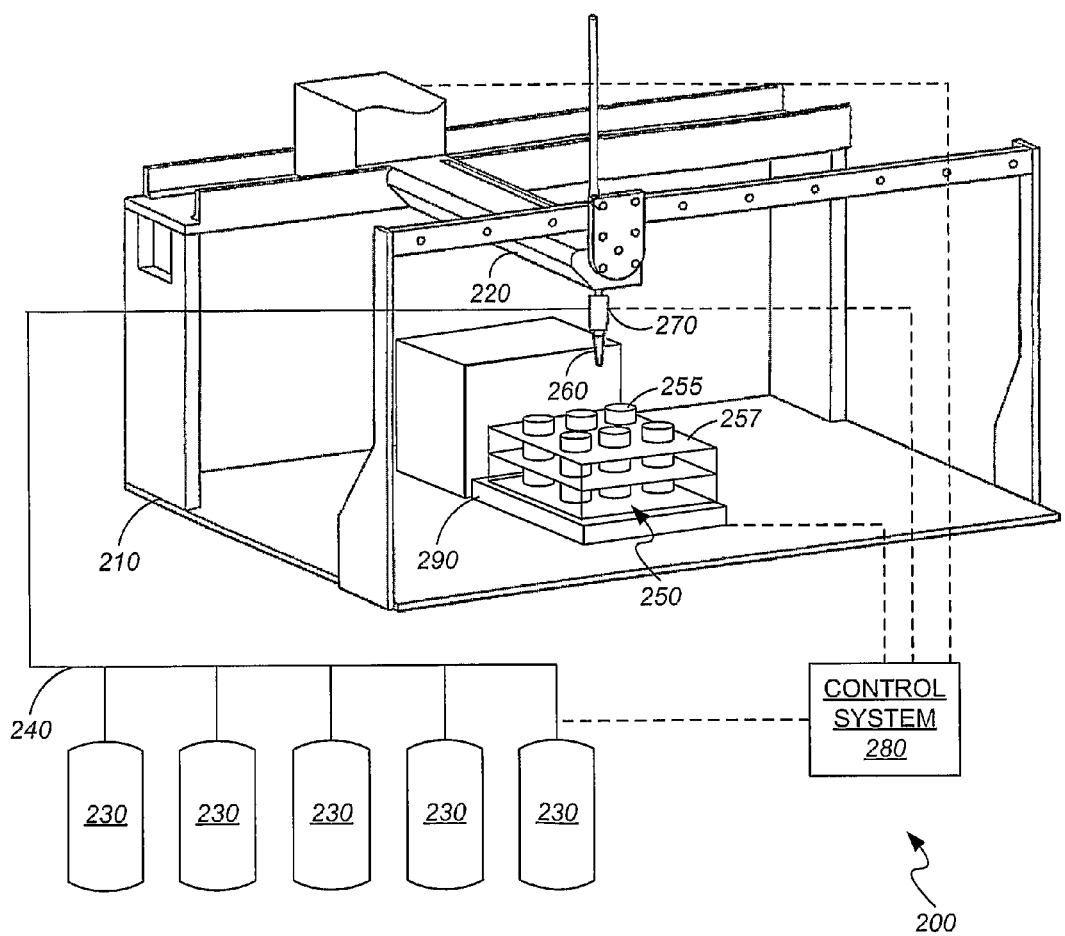
FIG. 2 illustrates one embodiment of a backpressure dispensing system suitable for implementing the method shown in FIG. 1.

Referring to FIG. 2, a liquid dispensing system 200 that can be used to implement method 100 according to one aspect of the present invention includes a liquid transport device 210 having an arm 220. System 200 is adapted for transferring liquids from one or more source reservoirs 230, by means of a network of fluid conduits 240, to one or more locations in a destination substrate 250. To that end, system 200 further includes a fluid outlet 260, mounted on arm 220. A dispense valve 270 in fluid outlet 260 is activated by control system 280, which includes a programmable microprocessor or other suitable processing device, to dispense quantities of liquids transported from source reservoirs 230 along a flow path defined by conduit network 240 to fluid outlet 260. Control system 280 can also be configured to control the motion of arm 220 in order to position dispense outlet 260 at any desired destination location 250 on the deck of robot 210. To provide for monitoring and feedback, system 200 can also include a balance 290, configured to support destination substrate 250 and to provide signals to control system 280 representing the mass of liquid being dispensed into destination locations 250. Control system 280 can be configured to use these signals to control the operation of dispense valve 270, and thereby provide for the dispensing of precise amounts of liquid components to destination locations 250 as will be described in more detail below.

In one embodiment, source reservoirs 230 include a plurality of vessels capable of maintaining an internal pressure in the range from 0 to 100 psi. Each source reservoir 230 is coupled in fluid communication with conduit network 240 through a valve, which can be controlled by control system 280 to introduce the pressurized liquid contents of the source reservoirs into conduit network 240. In general, the source reservoirs have a volume in the range from about 0.1 to about 50 liters, although the source reservoirs 230 can be provided in any convenient size (or a variety of different sizes) depending on the particular application and liquid components in question. Any commercially-available pressure vessels can be used, such as the 626DTH tank reservoir, available from EFD, Inc. The number of source reservoirs used may vary, depending on the number (and type, as discussed below) of liquid components to be used in dispensing operations performed by system 200. In typical embodiments, system 200 can be configured with at least five, at least 10, at least 15 or at least 20 or more source reservoirs, each containing a corresponding, different liquid component to be dispensed by system 200. In addition, system 200 can be provided with one or more system fluid reservoirs and a compressed air reservoir containing a system fluid, such as a solvent, and compressed air (or inert gas), respectively, that can be used to clean and dry conduit network 240.

The source reservoirs are preferably pressurized with an inert gas (i.e., a gas that does not interact with or dissolve in the relevant liquid component to any appreciable extent). Each reservoir can be equipped with its own pressure regulator and over-pressure valve and can be pressurized to a different pressure based, for example, on flow characteristics (e.g., viscosity, desired flow rate) of the corresponding liquid component. Alternatively, each source reservoir can be pressurized to the same operating pressure. In some embodiments, source reservoirs 230 can be maintained at pressure throughout the course of a set of experiments (e.g., each source reservoir 230 can be equipped with a computer-controlled regulator, and control system 280 can adjust the pressure during the course of dispensing operations based on the observed mass flow rate to maintain each liquid component in an ideal flow range regardless of viscosity and flow characteristics); alternatively, source reservoirs 230 and control system 280 can cooperate to pressurize source reservoirs on an as-needed basis—for example, pressurizing a particular source reservoir 230 immediately before the liquid component stored in the source reservoir is to be dispensed, by means of individual pressure manifolds or a pressurized tip. In some embodiments, the source reservoirs 230 can be positioned on the deck of robot 210. Alternatively, particularly in applications involving a large number of source reservoirs and/or large volume reservoirs, the source reservoirs 230 can be positioned at a location off of the robot deck but otherwise in proximity to robot 210. Optionally, the source reservoirs 230 and the conduit network 240 can be heated to lower the viscosity of the liquid components contained therein and to therefore improve the accuracy of the dispensing.

Substrates suitable for the present invention include one or more locations (e.g., wells) for receiving liquid components, which locations may be formed in variety of shapes and configurations. Thus, for example, wells may square, rectangular, cylindrical, straight, angular, or curved, or any other shape, and may be formed in any depth or size. Wells may be defined by walls of a member or substrate into which the wells extend. Alternatively, a member or substrate may have raised portions to define wells. Moreover, wells may be defined within a single continuous portion of a substrate or the substrate may comprise more than one portion or member that include the destination locations/wells, which portion or member may be maintained separately or may come together as an assembly of wells.

A substrate may also include one or more racks or other suitable support members, each supporting one or more vials, tubes or other containers that define the destination locations. Thus, in the embodiment of FIG. 2, destination substrate 250 comprises an array of vials 255 in a rack 257, although the destination substrate 250 (and its constituent destination locations) can take other forms. The wells can be formed from any convenient material, such as glasses, ceramics, plastics, or stainless steel. Preferably, the wells (or at least the internal surfaces thereof) are formed from materials that are inert to the liquid components and mixtures involved in the particular application. In the embodiment shown in FIG. 2, the destination substrate tales the form of a rack of six vials having a volume in the range from about 5 to about 500 milliliters. In other embodiments, the number and arrangement of the vessels or receptacles forming the destination array can vary. Thus, in particular embodiments, the destination substrate can include, for example, 12 or more, 24 or more, 48 or more, or 96 or more destination vials/locations.

Transport device 210 includes a robot (e.g., a Tecan® robot) having an arm 220 mounted on a rail for movement along a horizontal X-axis. As shown in FIG. 2, fluid outlet 260 (and dispense valve 270) is mounted on a vertical rod that is supported on the arm for horizontal movement with respect to the arm along a Y-axis and for vertical movement with respect to the arm 220 along a Z axis corresponding to the longitudinal axis of the rod. In the embodiment of FIG. 2, the Z-axis corresponds to the central vertical axis of fluid outlet 260, but these two axes could be offset. Although the robot 210 shown in FIG. 2 has only a single arm 220, in other embodiments the robot can be configured with two or more arms, as will be discussed in more detail below. Similarly, the arm 220 can be configured with additional tools for dispensing components (e.g., solids, including powders, liquids, or gasses) or for performing other operations, as will also be discussed below. Optionally, to accommodate the use of balances having higher accuracy but lower range and/or to make it possible to use a single balance (or a few balances) with many substrates, one or more of the robot arms can be configured with a gripping device, with which the robot can grasp and transfer a substrate (e.g., a vial) to and from the balance for weighing after each dispense. The robot 210 is programmable in conventional fashion to move fluid outlet 260 to any desired location on the robot deck. In other embodiments, other types of conveying devices may be used to transport the fluid outlet. Alternatively, fluid outlet 260 may remain fixed, and the destination substrate 250 may be moved relative to fluid outlet 260—for example, by one or more conveyors, turntables or other mechanisms.

As noted above, conduit network 240 includes a network of fluid conduits that are in fluid communication with a plurality of inlets that may be associated with individual source reservoirs 230, and defines a flow path from each of these inlets to fluid outlet 260 and dispense valve 270. The fluid conduits can be formed from any convenient material, such as stainless steel, glasses, or plastics—preferably, a material or materials that are inert to (e.g., not reactive with) the liquid components in question. In typical embodiments, the conduits have internal diameters in the range from about 2 mm to about 13 mm, with the choice of a particular diameter or diameters depending on the path length of the conduit and the particular characteristics (e.g., viscosity, desired flow rate) of the liquid components and dispensing operations involved in the particular application.

In particular embodiments, the inlets to conduit network 240 can take the form of valves that can be opened and closed under the control of control system 280 to allow the liquid components to flow from their associated source reservoirs 230 into conduit network 240 by action of the pressure in the source reservoir. The choice of the particular type of valve used in these embodiments may depend upon the application, and in particular on the characteristics of the liquid components and dispensing operations in question. In general, any conventional valve or other switchable fitting can be used, including, for example, diaphragm valves, needle valves, ball valves, gate valves, pistons, solenoids and the like. Preferably, the valve should have a low internal volume and few, if any, flow restrictions.

As noted above, conduit network 240 defines a flow path from each of the inlets to fluid outlet 260 and dispensing valve 270. In particular implementations, conduit network is configured with substantially no dead space in the flow path from any of the inlets to the fluid outlet with substantially no dead space (or restrictions) in the flow. The minimization/elimination of dead space in the flow path makes it possible to clean the conduit network after each dispense, as will be discussed in more detail below, such that each liquid component can traverse the conduit network from its respective inlet to the fluid outlet without contamination by or mixing with any previously-dispensed liquid component. This facilitates the precise formulation of liquid mixtures according to a predetermined recipe, particularly where highly-viscous liquid components are used.

Figure 3:
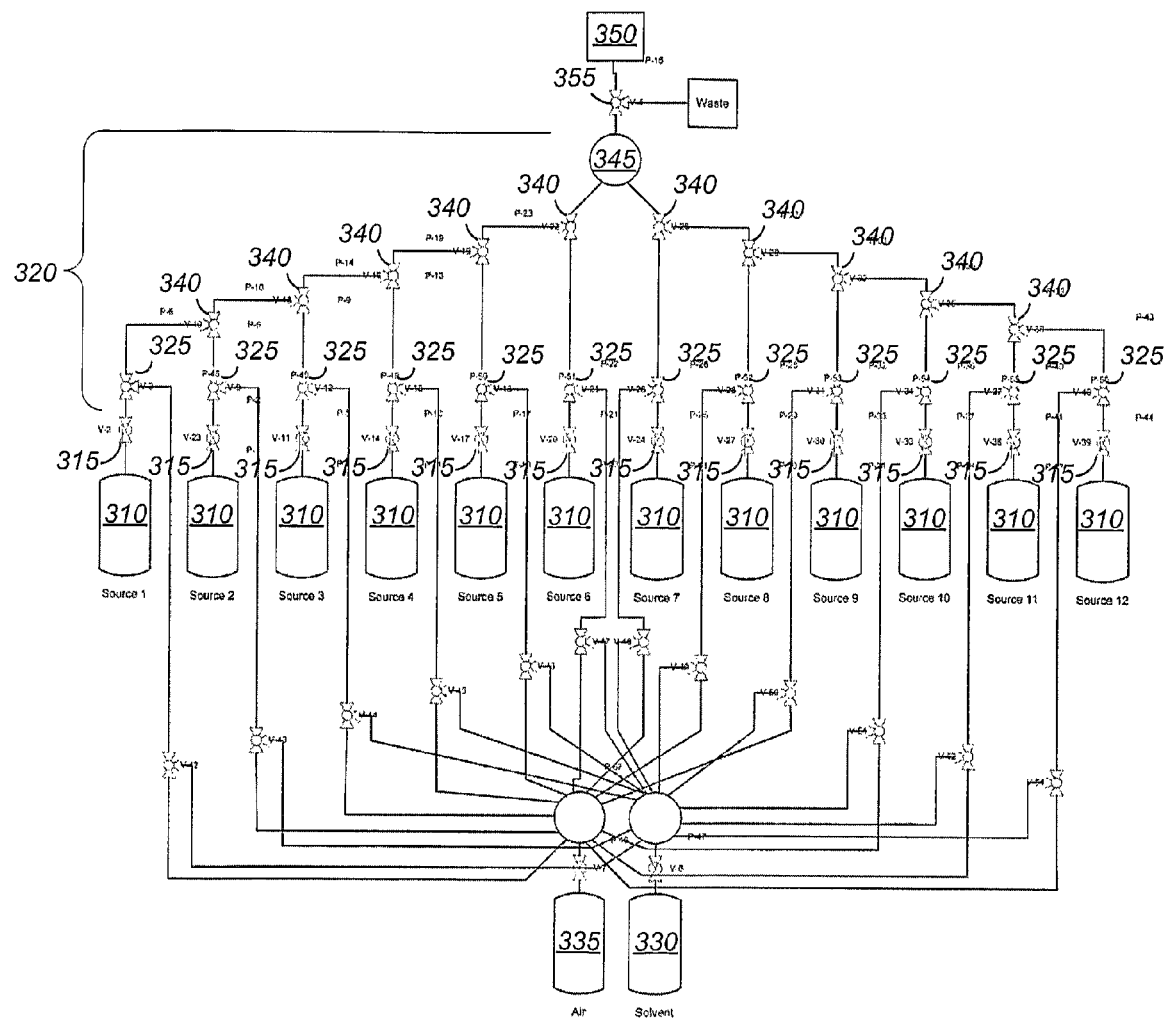
FIG. 3 is a block diagram schematically illustrating one embodiment of a conduit network suitable for use in the backpressure dispensing system shown in FIG. 2.

One embodiment of a suitable conduit network according to one aspect of the invention is illustrated in the context of a dispensing system 300 schematically shown in FIG. 3. As shown, dispensing system 300 includes 12 source reservoirs 310, each equipped with a corresponding outlet valve 315. The conduit network 320 includes a series of 12 inlet valves 325 associated with each source reservoir 310/outlet valve 315. In the embodiment shown, each of the inlet valves 325 is a three-way valve that is in fluid communication with two cleaning fluid reservoirs—a solvent reservoir 330 and a compressed air reservoir 335 in addition to the associated source reservoir 310. The flow lines in conduit network 320 extend from inlet valves 325 to a second series of three-way valves 340, where the flow lines from neighboring source reservoirs (or from neighboring valves 340) join, such that conduit network 320 defines a hierarchical network of fluid conduits. Ultimately, the flow lines join at a final three-way valve 345, from which a common flow line extends to a dispense valve 350. Optionally, the liquids traveling through conduit network 320 can be dispensed to waste via 3-way valve 355.

In operation, control system 280 identifies a first liquid component to be dispensed using system 300. Control system 280 then activates the outlet valve 315 and conduit network inlet valve 325 associated with the appropriate source reservoir 310, which causes the liquid component to flow out of the source reservoir 310 under pressure and enter conduit network 320. The liquid component then flows through the appropriate intermediate valves 340, 345 to dispense valve 350. Control system activates dispense valve 350 to dispense a desired quantity of the liquid component into a destination location (e.g., a vial or other container in a destination substrate array as discussed above). By controlling the time interval during which dispense valve 350 is open, control system 280 can precisely control the amount of the liquid component that is dispensed at the destination location. Optionally, if the liquid component is to be dispensed at another destination location, control system 280 can cause robot 210 to reposition fluid outlet 260 and reactivate dispense valve 350 to dispense a metered quantity of the liquid component a the new location.

When all of the desired dispenses of the liquid component are complete, control system 280 can dispense any remaining amount of the liquid component that remains in conduit network 320 to waste (e.g., by activating waste valve 355, or by repositioning fluid outlet 260 to a waste location and activating dispense valve 350 to dispense the remaining liquid component). Control system 280 then flushes conduit network 320 by introducing a cleaning fluid from solvent reservoir 330 into the conduit network through the previously-activated inlet valve 325 (i.e., the inlet valve through which the just-used liquid component entered network 320). By activating the intermediate valves 340, 345 through which the just-used liquid component traveled, control system 280 causes the cleaning fluid to flush the line through which the liquid component passed, minimizing or eliminating the chance that any subsequently-dispensed liquid component will mix with or be contaminated by the previous liquid component in the conduit network. After the cleaning fluid has traversed the conduit network, it is dispensed to waste as discussed above. In a similar fashion, control system 280 can then remove any trace of the cleaning solvent from conduit network 320 by flushing the lines with a cleaning gas from compressed air reservoir 335. Subsequent liquid components can then be dispensed as described above without risk of contamination.

Figure 4:
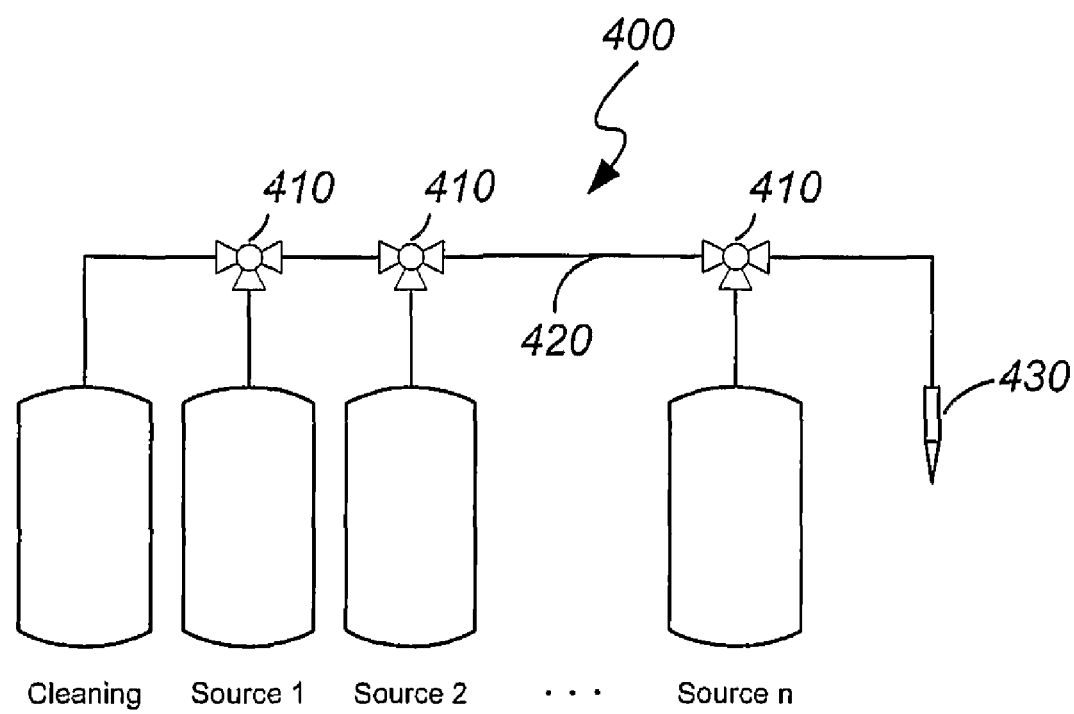
FIG. 4 is a block diagram illustrating an alternative embodiment of a conduit network for use in the system of FIG. 2.

In a preferred embodiment, inlet valves 325 and intermediate valves 340, 345 are three-way ball valves, which can be cleaned easily and do not expose the valve rotor to additional fluids for contamination, although other types of valves can be used. Although a particular hierarchical conduit network design is illustrated in FIG. 3, the conduit network can be provided in other configurations, such as a manifold. Thus, for example, in an alternative embodiment a conduit network 240 can be implemented as a valve array 400, illustrated in FIG. 4, in which a plurality of inlet valves 410 access a single flow path 420 that leads to a dispense valve 430. In this embodiment, cleaning fluid is introduced into conduit network 400 at a location (e.g., through one or more of the inlet valves 410 or through a separate inlet valve) that provides access to flow path 420 upstream of all of the inlet valves 410, such that cleaning fluid can flow past each inlet valve 410 during the cleaning cycle. More generally, the conduit network should include minimal dead space and should not contain any restrictions in the line which might introduce a significant pressure drop in the system. The inlet and any intermediate valves can be pneumatically controlled or solenoids driven by a computer (e.g., control system 280).

Dispense valve 270 can be implemented as any conventional type of fast-actuating valve that can be controlled by control system 280. In typical embodiments, the dispense valve 270 is configured to provide for actuation times of less than 100 milliseconds, preferably in the range of from about 1 millisecond to about 10 milliseconds, with a cycle rate of approximately 500/min. In one embodiment, dispense valve 270 can be a commercially available piston valve such as the Series 725HF high-flow valve, available from EFD, Inc.

As noted above, system 200 includes a weighing system comprising a balance 290, which operates to monitor the quantity of liquid dispensed at each location in the destination substrate 150 that is supported on the surface of balance 290. In particular, the destination substrate(s) 250 is precisely positioned on the surface of balance 290, such that the precise position of each destination location is known. During operation of system 200, balance 290 monitors the increasing weight of the destination substrate 250 as liquid is dispensed from fluid outlet 260 into each destination location 250 to provide a measurement of the amount of liquid being dispensed. Balance 290 can be of any conventional type (e.g., a precision electronic balance capable of communication with the control system 290) having suitable accuracy and capacity (e.g., readable to within 0.1 mg with a capacity of 1000 grams). Alternatively, the amount of liquid dispensed can be monitored in other ways.

As noted above, system 100 can include a cleaning subsystem to provide for cleaning of the various parts of the system—in particular, for flushing the conduit network and dispensing valve between dispenses to prevent contamination or mixing of the liquid components during dispensing. In typical embodiments, the system can include one or more additional reservoirs, such as the pressurizable reservoirs discussed above, charged with cleaning fluids and coupled to the conduit network to permit the introduction of the cleaning fluid into the conduit network to clean the entire flow path that will be encountered by a liquid component to be dispensed. The choice of cleaning fluid(s) may depend on the application, and in particular upon the identity and characteristics of the liquid components being dispensed. In particular embodiments, the cleaning fluid(s) can be, for example, water, aqueous or organic solvents, or gasses, such as air or inert gasses.

System 100 can also include an external enclosure that surrounds some or all of the components of the system. In some embodiments the use of an enclosure such as a glove box provides for the dispensing and mixing of air-sensitive liquid components in an inert atmosphere. In addition, the use of an enclosure can minimize undesirable air currents or other environmental factors that can adversely affect the accuracy of the balance 190 and/or otherwise disturb the liquid components or dispensing operation.

The systems and methods of the present invention can be used to form a plurality of liquid mixtures from a plurality of liquid components. As used herein, liquid components are materials that are at least partly in the liquid phase, including, for example, pure liquids, solutions, suspensions, dispersions, emulsions, and the like. Liquid mixtures produced using the techniques described herein can be homogeneous or heterogeneous blends of two or more liquid components, and can include two or more materials that are substantially miscible or substantially immiscible relative to each other for a given condition. Liquid mixtures can also include two or more materials that differ in other characteristics, such as form, composition, processability, viscosity, pH, phase separation behavior, or the like. Moreover, such characteristics may render the materials immiscible or miscible relative to each other and/or compatible or incompatible relative to each other.

The liquid components can include a wide variety of materials, including but not limited to, metals, ceramics, composites, organic materials, inorganic materials, flocculated materials, colloids, non-volatile materials, soluble materials, combinations thereof and the like. The liquid mixtures typically include one or more base components (e.g., main ingredients), each of which may be present in volumes ranging from about 50% to about 90% of the total volume, and can include one or more additives, such as light or temperature stabilizers, colorants, performance enhancers, biocides, fungicides, flame retardants, viscosity modifiers, foaming agents, or the like, that are each present in volumes ranging from about 0.1% to about 5% of the total volume. In particular embodiments, the techniques described herein can be used in a high throughput and/or combinatorial research project exploring the preparation and/or optimization of liquid mixtures that may be useful in a variety of different applications, such as polymeric materials, lubricants, gels, adhesives, coatings, foodstuffs, cosmetics, beverages, lotions, creams, pharmaceuticals, inks, biological fluids, fuels and other petroleum products, additives, detergents, surfactants, shampoos, conditioners, other hair styling products, dyes, waxes, fuel cell electrolytes, and the like. When designing libraries of liquid mixtures in such high-throughput embodiments, one or more of the liquid components can be dispensed in a amounts specified by one or more mathematical relationships to amounts of the same or different liquid components used in the liquid mixtures—for example, a gradient of amounts across the locations of the destination substrate, or in a ratio to an amount or amounts of one or more other liquid components dispensed to the destination location. In one preferred embodiment, the systems and methods are used to dispense components for high throughput creation and screening of lubricant oil blends.

When all of the desired components have been dispensed at each of the destination locations (or some subset thereof), the components at each destination are mixed to provide a collection of liquid mixtures or blends. Any suitable technique for mixing at least liquids can be used. In general, energy is applied at each destination location to physically blend the components together. Typically, the energy is applied by a mechanical mixing, and more preferably by mixing that imparts shear flow, elongational flow or a combination thereof to mix the components. Examples of such mixing include, without limitation, periodic mixing (e.g., rotary mixing involving a mixing blade mounted on a rotor shaft, magnetic stirrers, beads, pellets or the like, or a combination of these), forcing the materials through a constricted volume (e.g., between opposing surfaces, such as the nip and roll of a mill, the screw and barrel of an extruder, a wall defining an orifice or the like), shaking, ultrasonic mixing, or other suitable pressure or force application. The mixing can be performed at any suitable temperature, and can involve subjecting the dispensed components to thermal treatment (e.g., heating, cooling or a combination of these) to assist in the mixing process.

Optionally, the mixing can include, or can be followed by, additional processing of the dispensed components and/or liquid mixtures (e.g., one or more of the mixtures can be heated and allowed to undergo a physical and/or chemical transformation, such as a chemical reaction). In particular embodiments, this subsequent processing can be performed in an effort to replicate temperature, time, pressure or other conditions that the liquid mixtures may encounter in a commercial or industrial environment.

The liquid mixtures can be screened using a variety of screening techniques. In some embodiments, the liquid mixtures are screened to characterize the liquid mixtures themselves. Alternatively, or in addition, the liquid mixtures can be screened to observe how the mixtures perform under certain conditions, and/or to identify optimal mixtures. The screening can include analyzing the liquid mixtures for any of a number of relevant characteristics, including for instance chemical composition, viscosity, turbidity, decomposition, or other physical properties of interest. In particular embodiments, the screening can include analyzing the liquid mixtures (either individually or in collections/libraries) using conventional characterization techniques, such as those employing beam radiation analysis (e.g., x-ray diffraction, high-throughput x-ray scattering, scattering from experimental systems, viscometry, failure or strength testing, adhesion testing, birefrigerance, rheo-optics, electron radiation, neutron radiation, sychotron radiation, or the like), infrared techniques (e.g., FTIR, IR detection or otherwise), thermal analysis techniques (such as differential scanning calorimetry, differential thermal analysis or the like), chromatographic techniques, resonance, spectroscopy, light scattering, spectrometry, microscopy, nuclear magnetic resonance, optical measurements, electrochemical measurements.

In some embodiments, temperature can be controlled at any point in the dispensing, mixing and/or screening process according to any of a variety of methods. As an example, gas (e.g., air) surrounding the source reservoirs and/or destination substrate can elevated or lowered to adjust temperature of the source components and/or resulting mixtures. As another example, the temperature of a destination substrate or an individual location thereon can be controlled to affect the temperature of the mixtures supported by that substrate or in that location. Exemplary heating devices for raising or lowering the temperatures of samples include heating elements, infrared (IR) lamps, thermoelectric elements, refrigeration systems and the like.

The use of closed-loop feedback as discussed above can provide for accurate dispensing of a wide variety of liquids accurately using a single system. In particular, in some embodiments the system is calibrated for each liquid component to provide for accurate dispensing. In general, it can be challenging to develop a system for dispensing liquids having a wide variety of characteristics—in particular, liquids having widely varying viscosities—because each material may perform differently. Additionally, system performance may drift over time due to equipment wear and environmental conditions. To compensate for any variation in performance, the system can use a balance to check and verify the dispense accuracy, as well as to correct for any errors that may occur during dispensing.

Figure 5:
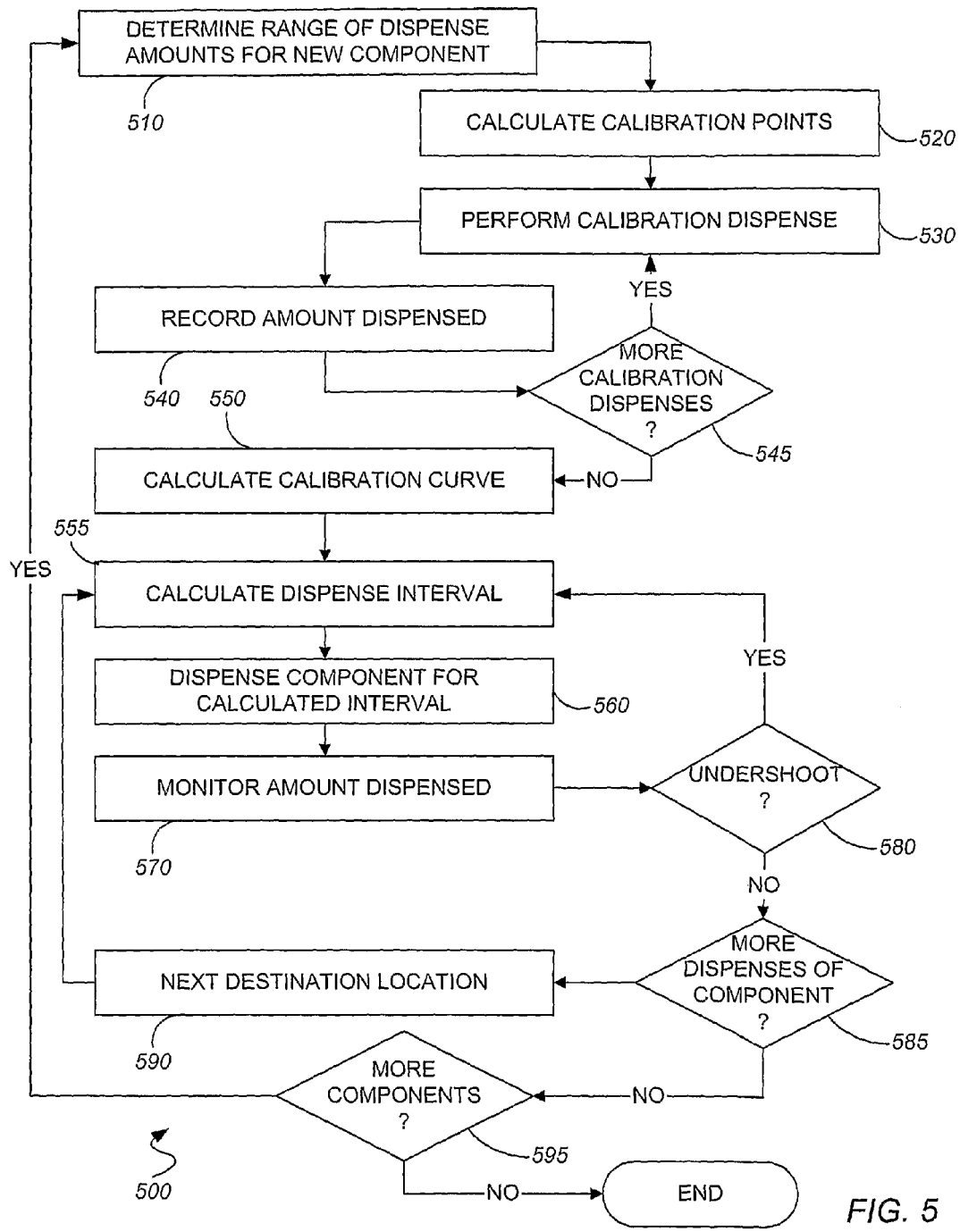
FIG. 5 is a flow diagram illustrating one embodiment of a liquid dispense calibration method according to one aspect of the invention.

In one embodiment, the system performs an initial calibration when a new liquid component material is to be dispensed. One embodiment of a method 500 for calibrating the system and dispensing a liquid component is illustrated in FIG. 5. Control system 280 analyzes the recipe(s) to be used for each liquid mixture and determines a range of amounts in which the component is to be dispensed (step 510). Control system 280 then calculates a set of calibration points that fall within and span the breadth of this range (step 520). Typically, the calibration points are calculated as target amounts (e.g., masses, volumes) and dispense intervals that correspond to the amount of time that is expected to be required for the dispense valve to dispense the target amount. In some embodiments, control system 280 identifies the appropriate dispense intervals based in part upon an estimated viscosity of the new liquid component, which may be supplied by the user. In typical embodiments, control system 280 calculates from six to twelve calibration points, although more or fewer points can be calculated, depending on the particular application.

To generate a calibration curve based on the calculated points, the system performs a series of dispenses of the new liquid component (step 530), activating the dispense valve to dispense the liquid component (e.g., into a waste location) for an amount of time corresponding to the appropriate calculated dispense interval. For each dispense, the system records the amount of the new liquid component that is actually dispensed during the dispense interval (step 540). Each dispense in the series corresponds to one of the calibration points, such that the first dispense is performed for a dispense interval expected to result in the delivery of a first target amount, the second dispense is performed for a second dispense interval expected to result in the delivery of a second target amount, and so forth. When the series of dispenses has been performed (the NO branch of step 545) and the actual dispense amounts recorded, the system calculates a calibration curve based on the dispense intervals and actual amounts (step 550). In some embodiments, the calibration curve may have linear and nonlinear regions. The calibration curve can be stored in a memory (e.g., a database) incorporated in or operatively coupled to control system 280, from which it can be retrieved for use in controlling subsequent dispensing operations involving the new liquid component.

Once the system has calculated the calibration curve, the new liquid component can be dispensed into the destination locations as desired. For each dispense, the system calculates a dispense interval based on the amount of the liquid component to be dispensed at the current destination location, and on the calibration curve (step 555). The system activates the dispense valve for this calculated dispense interval, and dispenses a corresponding quantity of the liquid component at the current destination location (step 560). In some embodiments, the system calculates this dispense interval to undershoot the amount to be dispensed, so that it does not dispense too much of the liquid component at the destination location. Based on the signals received from the balance indicating how much of the liquid component was actually delivered (step 570), control system 280 calculates how much more of the liquid component must be dispensed, again incorporating with a slight undershoot. This cycle continues until the amount dispensed is sufficiently close to the desired amount (e.g., within some predetermined error threshold or within the resolution of the dispense technology) (the NO branch of step 580). If more dispenses of the liquid component remain (the YES branch of step 585), control system 280 causes robot 210 to move the fluid outlet 260 to a new destination location (step 590) and repeats the process. If no more dispenses of the liquid component remain, the system can proceed to the next liquid component (step 595), including performing a calibration for that component, if no calibration has been performed.

The use of real-time monitoring of dispensed amounts also makes it possible to correct for any dispensing errors as mentioned above. In some embodiments, this correction can be implemented by normalizing the target mass for each liquid mixture in a library of mixtures based on the actual dispensed amount of one or more of the liquid components—that is, by recalculating the amount of each liquid component to be added to a given destination location to form a liquid mixture to satisfy a recipe that specifies the mixture composition based on relative percentages of the components that will make up the mixture. In particular, the target (total) amount for the mixture can be recalculated based on the actual dispensed amount for a specified component of the mixture. Thus, for example, the target amount can be normalized based on the actual dispensed amount for the component with the smallest desired mass (for which the dispense error may be expected to be greatest as a percentage of the amount dispensed). Similarly, if a relevant characteristic of the resulting liquid mixture is expected to have significant sensitivity to variations in the dispensed amount of any component (e.g., a component for which small variations in amount may have a large impact on the viscosity of the resulting liquid mixture), the target amount can be normalized based on the actual dispensed amount of such the component. In particular embodiments, the component upon which any such normalization will be based will be dispensed first into each destination location, so that the correct dispense amount for each of the other liquid components of the mixture to be dispensed at that location can be determined.

In another aspect of the present invention, the systems and methods can be implemented to provide for high-throughput dispensing in different dispensing regimes, and in particular embodiments to provide a single instrument that is capable of performing dispensing operations at both small and larger volumes (and potentially with low- and high-viscosity liquids). Thus, in some embodiments the systems and methods can incorporate two or more different types of dispensing technologies to dispense low- and high-volume components. For example, in one embodiment, backpressure dispensing technology, as discussed above in the context of FIGS. 1-4, can be used to dispense high-volume liquid components (e.g., base components that will be dispensed in volumes ranging from about 50% to about 90% of the total volume in one or more of the destination locations), while a syringe pump or positive displacement pipette can be used to dispense low-volume liquid components (e.g., additives that will be dispensed in volumes ranging from about 0.1% to about 5% of the total volume).

As noted above, the techniques described herein are typically used to prepare liquid mixtures that include one or more base components that make up a relatively large proportion of each mixture, and one or more additives that make up a relatively much smaller proportion of each mixture. The use of a high-volume technology to dispense components that will be dispensed in relatively larger amounts, or that represent a relatively large proportion of the liquids to be dispensed over a particular period of time (e.g., in preparing a particular sample, a particular library of samples, or a particular series of libraries), takes advantage of the faster high-volume technology to increase the efficiency of dispensing these components. Similarly, even if all components are to be dispensed in small volumes, high-volume and low-volume dispensing technologies can be used to increase dispensing efficiency by allocating the dispensing of common components (i.e., components that will be used in a relatively large number of dispenses) to the high-volume technology and the dispensing of uncommon components (i.e., components that will be used less frequently in the library design) to the low-volume technology.

In these embodiments, the systems and methods can be implemented with a robot having two or more arms, with each different dispensing technology being mounted on a dedicated arm. Alternatively, two or more types of dispensing technologies can be implemented on a single robotic arm. Optionally, additional dispensing technologies, such as solid (e.g., powder) dispensing technologies, can be implemented in the same system. Using these systems, the individual components can be delivered separately to different destination locations either sequentially or simultaneously. In one embodiment, the components are sequentially delivered to either a single destination location or, alternatively, to multiple destination locations. For example, in a system having two dispensing technologies mounted on one or more arms, two components can be delivered simultaneously to locations on the destination substrate. Alternatively, using this same system, a single component can be simultaneously delivered to two different destination locations (in the same or different amounts). In this instance, the same ingredient or, alternatively, two different ingredients can be delivered.

In general, backpressure dispensing technology can be implemented to dispense high-volume components as discussed above, while low-volume dispensing can be implemented using an aspirate/dispense technology that provides for direct aspiration and dispensing of samples. Low-volume components such as additives are often expensive, and can be available only in limited quantities. High-volume dispensing technologies such as the backpressure dispensing system discussed above may be disadvantageous for dispensing such components, because these techniques may require the transport of significant amounts of a given component that are not actually dispensed at the destination, due, for example, to the potentially lengthy conduit network that transports the components from their respective source reservoirs to the dispense valve as illustrated in FIG. 3. In some embodiments it may be possible to recirculate some portion of any excess amounts of components using this technology, but in typical embodiments at least some of the excess will be dispensed (or flushed) from the system as waste, as discussed above. Thus, it may be more efficient to dispense low-volume components using dispensing technologies in which the desired amount of the component is directly aspirated and dispensed to the destination location.

As noted above, two such technologies suitable for low-volume dispensing incorporate one or more positive displacement pipettes or syringe pumps in fluid communication with a dispensing tip or needle, which can be a heated tip to provide for aspirating and/or dispensing at elevated temperatures. The selection of a particular low-volume dispensing technology can be based on the particular application. Moreover, in some embodiments the techniques can be implemented using two or more different low-volume technologies (e.g., with both a positive displacement pipette and a syringe pump with dispensing tip), which can be mounted on a single robot arm or on separate arms. In such embodiments, the user can choose the low-volume technology that may be most suitable for each particular dispensing operation.

Figure 6:
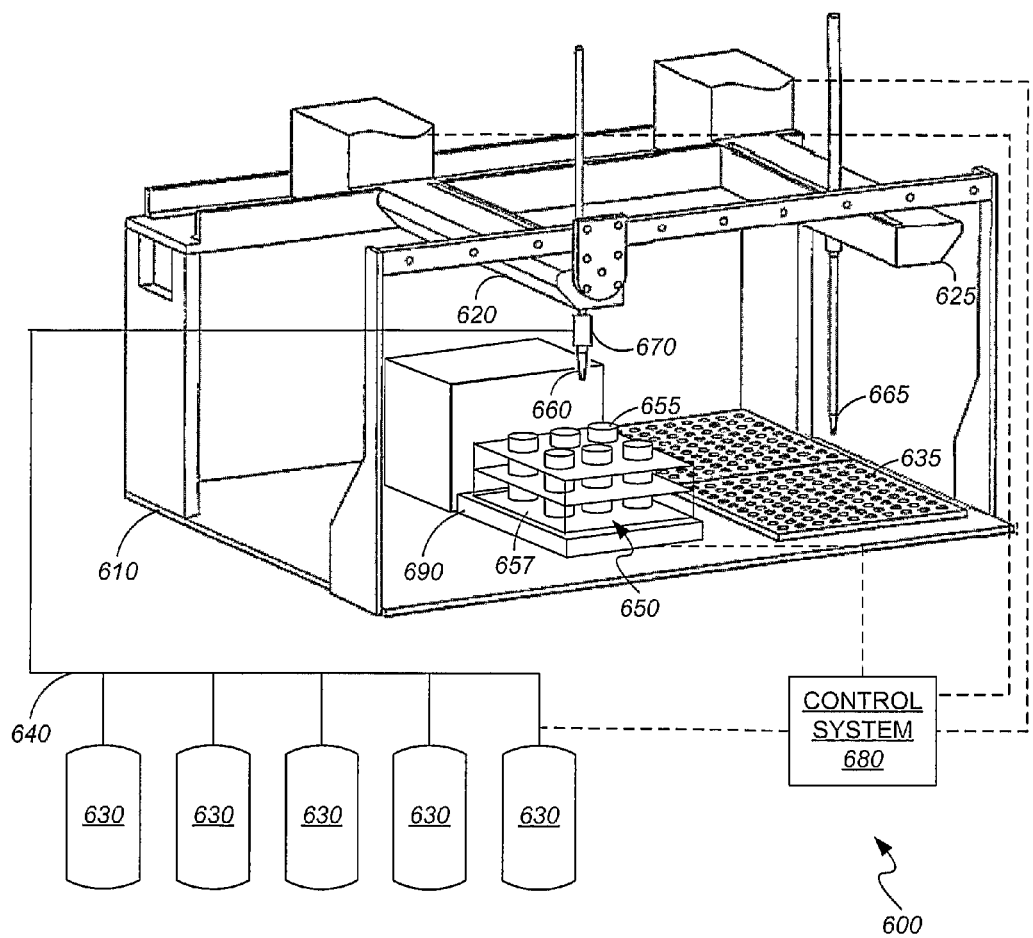
FIG. 6 illustrates one embodiment of a dual-dispensing-technology dispensing system according to one aspect of the present invention.

In one embodiment, a dual-technology dispensing system 600, illustrated in FIG. 6, includes a robot 610 having a backpressure dispensing subsystem including a first fluid outlet 660 incorporating a dispensing valve 670 mounted on a first robot arm 620. A positive displacement pipette 665 (or dispensing tip coupled to a syringe pump) is mounted on a second robot arm 625. Liquid components to be dispensed are provided in two sets of source reservoirs. A first set of source reservoirs includes one or more pressurizable reservoirs 630 suitable for use in backpressure dispensing as discussed above, which reservoirs are loaded with liquid components that will be dispensed in large volumes. A second set of one or more source reservoirs (well arrays 635) is loaded with liquid components that will be dispensed in smaller volumes. The reservoirs in the second set of source reservoirs can be any containers from which liquid components can be withdrawn using the particular low-volume dispensing technology in question—for example, bottles, flasks or vials from which liquid components can be aspirated using a syringe pump or positive displacement pipette. Optionally, some or all of the first set of reservoirs 630 and the second set of reservoirs 635, the conduit network 640, and the dispensing tip 665 can be heated to maintain the corresponding liquid components at elevated temperatures, thereby reducing viscosity during the dispensing operations and thereby improving the dispensing accuracy; thus, for example, the second set of reservoirs can be provided as a collection of vials positioned in a heated block on the deck of the robot.

Liquid components from both sets of source reservoirs can be dispensed using the appropriate dispensing technology (selected, e.g., based on the particular volume of each liquid component to be dispensed) to destination locations 650 in a single destination substrate or set of substrates (e.g., vials 655 in a rack 657 or arrangement of racks as discussed above). In general, the order in which the components (or types of components) are added is not narrowly critical. In some embodiments, the order in which the components are added can be specified as a part of a recipe dictating components to be dispensed and processing conditions to be applied at each library location, although particular embodiments may feature the addition of different components in varying, even arbitrary orders. Thus, for example, in some embodiments all high-volume components may be dispensed first and low-volume components thereafter. In other embodiments, this order of addition may be reversed, or dispensing of high- and low-volume components may be interspersed. The destination substrate(s) can be positioned on the surface of a balance 690 to provide for closed-loop feedback during the dispensing operations, which can include the calibration techniques discussed above, which techniques can be applied to either or both of the high-volume components and the low-volume components. The operation of the system can be fully or partially automated under the control of a control system 680 as discussed above.

As noted above, the backpressure dispensing techniques described herein are well-suited for rapidly and accurately dispensing large volumes of liquid components, and can also be advantageous for dispensing high-viscosity liquids. It should be noted, however, that low-viscosity components can be dispensed using high-volume techniques such as backpressure dispensing, and that high-viscosity components can be dispensed using low-volume techniques such as systems incorporating syringe pumps or positive displacement pipettes. Thus, for example, lubricant blending applications may call for blends incorporating a large volume of one or more base stocks, which base stocks may typically have relatively low viscosities, while additives such as viscosity modifiers, which are typically among the most viscous components, are added only in small amounts. Under these conditions, it may be advantageous to dispense the low-viscosity, large volume base stocks using, e.g., back-pressure dispensing techniques, while dispensing the highly viscous additives using a syringe pump or positive displacement pipette.

As discussed above, the systems and methods of the present invention can be operated in an automated mode under the direction of a controller, such as a programmable processor. In some embodiments, the programmable processor can run one or more software programs that implement some combination of library design functions, process automation functions, and data gathering and presentation functions. The library design functions can provide for the interactive definition by the user of a set of recipes that specify a composition for each of a plurality of liquid mixtures, such as lubricating oil blends, in a library of liquid mixtures. The composition of each of the liquid mixtures can be specified in the form of an amount of each of a plurality of liquid components to be dispensed at each location on a destination substrate, where the locations correspond to members of the library of mixtures. Optionally, the library design functions can also permit the user to define one or more process conditions (e.g., heating, stirring, etc.) to be applied to one or more of the components, or to the combination of components, when the components have been dispensed at the destination locations. In some embodiments, the library design functions can be implemented in Library Studio® library design software available from Symyx Technologies, Inc., of Santa Clara, Calif.

The process automation functions can operate to receive library design information generated by the library design functions, and translate the recipes into commands suitable for controlling a robot or other instrumentation to dispense and process the liquid components as specified in the library design. For example, a recipe generated by the library design functions may specify that a particular liquid mixture is to be prepared by dispensing specific amounts of a first component and a second component at a particular destination location, where the first and second components are stored in a first source reservoir and a second source reservoir, respectively. The process automation functions can receive this information, and direct the liquid-handling robot to obtain the specified amounts from the first and second source reservoirs (e.g., by aspirating the first and second components from their respective reservoirs using a syringe pump, or by drawing the components in to a conduit network of a backpressure dispensing system as discussed above. The process automation functions can then direct the liquid handling robot to translate one or more dispensing outlets (e.g., heated tips, positive displacement pipettes, dispense valves) to the desired destination location and dispense the components in the specified amounts. Likewise, the process automation functions may provide for controlling post-dispense processing and/or analysis, in like manner. And the process automation functions can also operate to control screening instrumentation to analyze and/or characterize the liquid mixtures. In some embodiments, the process automation functions can be implemented in Impressionist® and/or Epoch® software available from Symyx Technologies.

The data gathering and presentation functions can operate to acquire and store experimental data resulting from the dispensing, processing and/or screening, and to process and present the experimental data to the user. In some embodiments, the data gathering and presentation functions can be implemented in Epoch® and PolyView® software available from Symyx Technologies.

The functional operations described in this specification can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. The essential elements of a computer are a processor for executing instructions and a memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the functional operations can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

A number of embodiments of the invention have been described. Nevertheless, it will be understood that various modifications may be made without departing from the spirit and scope of the invention. Accordingly, other embodiments are within the scope of the following claims.

What is claimed is:

1. A system for dispensing fluids, the system comprising:
a liquid handling robot having one or more robotic arms;
a plurality of source reservoirs, each of the plurality of source reservoirs containing a liquid component;
one or more conduit networks defining one or more flow paths from one or more of the plurality of source reservoirs;
one or more destination substrates having one or more destination locations for receiving liquid components to prepare one or more liquid mixtures;
a plurality of fluid outlets mounted on the one or more robotic arms, each of the fluid outlets being configured to receive liquid components from one or more of the source reservoirs, the fluid outlets comprising a first fluid outlet configured to dispense the received liquid components into one or more of the destination locations according to a high-volume dispensing system and a second fluid outlet configured to dispense the received liquid components into one or more of the destination locations according to a low-volume dispensing system; and
a control system programmed to control the liquid handling robot and the first and second fluid outlets to cause the system to dispense the liquid components at the one or more destination locations.

2. The system of claim 1, wherein:
the high-volume dispensing system comprises a back-pressure dispense system wherein the first fluid outlet comprises a dispense valve in fluid communication with a first conduit network of the one or more conduit networks, the first conduit network comprising a plurality of inlets, each of the plurality of inlets being associated with one of a first plurality of the source reservoirs, each of the first plurality of source reservoirs containing a first liquid component and maintaining an elevated pressure for forcing the corresponding liquid component to exit the first source reservoir, the first conduit network defining a flow path from each of the plurality of inlets to the first fluid outlet, the first fluid outlet being positionable using the one or more robotic arms to dispense the first liquid components through the dispense valve into any of the one or more destination locations.

3. The system of claim 2, wherein:
the low-volume dispensing system comprises an aspirate/dispense system.

4. The system of claim 3, wherein:
the second fluid outlet comprises or is in fluid communication with a positive displacement pipette, the positive displacement pipette being in fluid communication with a second plurality of the plurality of source reservoirs, the second plurality of source reservoirs containing a plurality of second liquid components, the positive displacement pipette being operable to withdraw one or more of the second liquid components from the second source reservoirs and to dispense the withdrawn second liquid components at the one or more destination locations through the second fluid outlet.

5. The system of claim 2, wherein:
the first source reservoirs are independently pressurized to provide for a target flow rate of the first liquid components at the dispense valve.

6. The system of claim 2, wherein:
the control system is programmed to cause the dispensing of quantities of each of a plurality of the first liquid components into each of a plurality of the destination locations by, sequentially for each of the plurality of first liquid components, activating the inlet associated with the corresponding first source reservoir to introduce the first liquid component into the first conduit network, positioning the first fluid outlet at one or more of the destination locations, activating the dispense outlet to dispense a quantity of the first liquid component at the one or more destination locations, and flushing the first conduit network to prevent contamination of subsequent first liquid components by the first liquid component.

7. The system of claim 2, wherein:
the first conduit network comprises a plurality of three-way valves configured to define a hierarchical flow path from each of the plurality of inlets to the first fluid outlet, the conduit network having substantially no dead space in the hierarchical flow path from any of the plurality of inlets to the first fluid outlet.

8. The system of claim 2, wherein the control system is programmed, before dispensing a given first liquid component of the plurality of first liquid components, to generate a calibration for the given first liquid component by:
determining a range of volumes of the given first liquid component to be dispensed to locations in the one or more destination locations;
performing a plurality of dispenses of the given first liquid component, including, for each of the plurality of dispenses, activating the dispense valve for a time period corresponding to a volume in the determined range of volumes;
measuring a quantity of the given first liquid component dispensed in each of the plurality of dispenses; and
calculating a calibration curve for the given first liquid component based on the time periods and the measured quantities of the given first liquid component for each of the plurality of dispenses;
wherein the control system is programmed to control the dispense valve by, for each destination location into which the given first liquid component will be dispensed, calculating a dispense interval based on a desired quantity of the given first liquid component and the calibration curve and activating the dispense valve for the calculated dispense interval to dispense the given first liquid component.

9. The system of claim 8, wherein the control system is programmed to control the dispense valve to dispense the given first liquid component by:
activating the dispense valve for a first dispense interval corresponding to a first desired quantity of the given first liquid component that is less than a target quantity of the given first liquid component and measuring a quantity of the given first liquid component dispensed during the first dispense interval;
calculating a second dispense interval based on the measured quantity and the target quantity of the given first liquid component, the second dispense interval corresponding to a second desired quantity of the given first liquid component, the second desired quantity being less than the difference between the target quantity and the first desired quantity;

activating the dispense valve for the second dispense interval and measuring a quantity of the given first liquid component dispensed during the second dispense interval; and repeating the calculating and the activating until an amount of the given liquid component that is within a predetermined amount of the target quantity of the given first liquid component is dispensed.

10. The system of claim 1, wherein:

the plurality of source reservoirs comprises a cleaning fluid reservoir in fluid communication with first conduit network, the cleaning fluid reservoir being positioned and configured to introduce a cleaning fluid into the first conduit network to flush the flow path from any one of the plurality of inlets.

11. The system of claim 1, wherein:

the control system is programmed to control the dispensing of liquid components based on a measured quantity of liquid components being dispensed at the one or more destination locations.

12. The system of claim 11, wherein:

the system includes one or more balances configured to support the destination substrates, the control system being configured to receive, from the one or more balances, signals representing the measured quantity of liquid components being dispensed at the one or more destination locations.

* * * * *